United States Patent [19]

Nakamura et al.

[11] Patent Number: 5,294,444

[45] Date of Patent: Mar. 15, 1994

[54] TRANSPARENT OR SEMI-TRANSPARENT COSMETIC COMPOSITION

[75] Inventors: Mami Nakamura, Kanagawa; Seiji Honma, Chiba, both of Japan

[73] Assignee: Kao Corporation, Tokyo, Japan

[21] Appl. No.: 796,685

[22] Filed: Nov. 25, 1991

[30] Foreign Application Priority Data

Nov. 26, 1990 [JP] Japan .................. 2-322081

[51] Int. Cl.$^5$ .................. A61K 7/06; A61K 7/09; A61K 7/11; A61K 31/74
[52] U.S. Cl. .................. 424/401; 424/70; 424/71; 424/78.03; 514/844; 514/845; 514/846; 514/847; 514/848
[58] Field of Search .................. 424/70, 71, 78.03, 401; 514/844, 845, 846, 847, 848

[56] References Cited

U.S. PATENT DOCUMENTS

| | | | |
|---|---|---|---|
| 4,009,256 | 2/1977 | Nowak, Jr. et al. | 424/70 |
| 4,247,538 | 1/1981 | Barker | 424/70 |
| 4,294,728 | 10/1981 | Vanlerberghe et al. | 424/70 |
| 4,450,091 | 5/1984 | Schmolka | 424/70 |
| 4,507,280 | 3/1985 | Pohl et al. | 424/70 |
| 4,560,500 | 12/1985 | Wiegers | 424/70 |
| 4,736,756 | 4/1988 | Grollier | 424/70 |
| 4,867,971 | 9/1989 | Ryan et al. | 424/70 |
| 5,089,257 | 2/1992 | Schrader et al. | 424/70 |

FOREIGN PATENT DOCUMENTS

| | | |
|---|---|---|
| 0227994 | 8/1987 | European Pat. Off. . |
| 0277641 | 8/1988 | European Pat. Off. . |
| 0349150 | 1/1990 | European Pat. Off. . |
| 0398272 | 11/1990 | European Pat. Off. . |
| WO80/01144 | 6/1980 | PCT Int'l Appl. . |
| 2213723 | 8/1989 | United Kingdom . |

OTHER PUBLICATIONS

Patent Abstracts of Japan, vol. 6, No. 7, (C-87) (885), Jan. 16, 1982, & JP-A-56-123-210, Oct. 19, 1981, M. Masuda, "Transparent Aromatic Gel Composition".

*Primary Examiner*—Thurman K. Page
*Assistant Examiner*—C. Azpuru
*Attorney, Agent, or Firm*—Oblon, Spivak, McClelland, Maier & Neustadt

[57] ABSTRACT

A cosmetic composition is provided comprising (A) 0.05-30% by weight of an amphiphatic lipid, (B) 0.05-30% by weight of a nonionic surfactant, (C) 1-50% by weight, based on (b), of an ionic surfactant, and (D) 40-99% by weight of an aqueous medium, wherein said composition is transparent or semi-transparent, and wherein the ratio of (A)/[(B)+(C)] is 0.2-10, which is beautifully transparent or semi-transparent, and in which the amphiphatic lipids are stably microdispersed.

20 Claims, No Drawings

TRANSPARENT OR SEMI-TRANSPARENT COSMETIC COMPOSITION

TECHNICAL FIELD

This invention relates to a cosmetic composition in which amphiphatic lipids are stably microdispersed in an aqueous medium, and which exhibits a transparent or semitransparent appearance.

BACKGROUND ART

The water content of the stratum corneum decreases as the skin becomes more rough, dry, or aged. To obtain a pleasant feel for the skin, or to obtain an attractive outerlayer of the skin, various moisture retaining agents or oils are often incorporated into cosmetic compositions. Oils tend to increase the water content of the stratum corneum by occlusion of the skin surface thereby softening the stratum corneum. On the other hand, aqueous moisture retaining agents tend to increase the water content of the stratum corneum because of their water retaining ability, also resulting in a softening of the stratum corneum. This is why cosmetic compositions containing various oils or aqueous moisture retaining agents, improve the feel of the skin and the skin's appearance. However, oils have the problem that they tend to be greasy or cause a skin shine. Aqueous moisture retaining agents are likely to be washed away with water, resulting in a short-lived cosmetic effect.

Intercellular lipids, are found in the intercellular portions of the stratum corneum, and form stratified structures which aid in the adhesion of the stratum corneum cells, and in the hydration of the stratum corneum. Such lipids, extracted from the skin have been used in cosmetic compositions instead of oils or aqueous moisturizing agents, (Japanese Laid Open Patent Application Nos. 62-29508/1987, 62-120308/1987). Likewise synthetic compounds having analogous structures to intercellular lipids have also been used for similar purposes (Japanese Laid Open Application No. 62-228048/1987, and U.S. Pat. No. 4,778,823).

Amphiphatic lipids, such as the intercellular lipids, are solid at room temperature (25° C.) and when used in cosmetics are incorporated in admixture with the oils and/or emulsifying agents, or are dissolved in large amounts of surfactant.

Opaque, white emulsions are obtained simply by mixing the lipids with the oils and/or emulsifiers, although it is difficult to incorporate intercellular lipids stably into cosmetic compositions wherein the lipids are in high concentration.

Transparent cosmetics are obtained by the use of a large amount of surfactant and lipids. Unfortunately large amounts of surfactant, tends to interfere with the function of the amphiphatic lipids, sometimes resulting in skin irritation due to the surfactants.

It would be desirable, therefore, to provide a cosmetic composition which does not irritate the skin, but which contains the amphiphatic lipids in a stable and clear transparent or semi-transparent condition.

DISCLOSURE OF THE INVENTION

Accordingly, it is an object of this invention to provide a transparent, or semi-transparent cosmetic containing amphiphatic lipids, which is non-irritating and which is nevertheless stable.

This and other objects of the invention as will become more apparent by the following description have been achieved by the use of a relatively small quantity of nonionic surfactant in combination with an ionic surfactant. The resulting cosmetic composition is found to be beautifully transparent or semi-transparent, and the amphiphatic lipids are found to be stable and microdispersed.

Specifically, a cosmetic composition has been provided which comprises:

(A) 0.05-30% by weight of an amphiphatic lipid,
(B) 0.05-30% by weight of a nonionic surfactant,
(C) 1-50% by weight, based on (b), of an ionic surfactant, and
(D) 40-99% by weight of an aqueous medium, wherein said composition is transparent or semi-transparent, and wherein the ratio of (A)/[(B)+(C)] is 0.2-10.

BEST MODE FOR CARRYING OUT THE INVENTION

In this invention, the cosmetic composition which has 1-1500 ppm of turbidity is referred to as transparent or semi-transparent. Turbidity is measured using purified Kaolin as a standard in aqueous solution (1 ng/liter) of 1 ppm as measured by a Turbidimeter.

An amphiphatic lipid (A) of this invention is defined as a lipid which has both hydrophobic group(s) and hydrophilic group(s) and can be dispersed in water but is not water soluble, and which is solid at room temperature (25° C.).

Suitable amphiphatic lipids include the higher alcohols, fatty acids, ceramides, glycoceramides, phospholipids, glycolipids, cholesterols, cholesterol fatty acid esters, and derivatives thereof.

Preferred are the amphiphatic lipids of the formula (I)

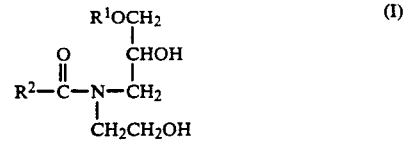

wherein $R^1$ is a hydrocarbon having 10 to 26 carbon atoms, preferably 12 to 22 carbon atoms, particularly preferably 14 to 18 carbon atoms, and $R^2$ is a hydrocarbon having 9 to 25 carbon atoms, preferably 11 to 21 carbon atoms, particularly preferably 13 to 17 carbon atoms.

The hydrocarbon chain may be either saturated or unsaturated, although a saturated chain is preferred. When the claim is unsaturated it may contain one or up to 5 points of unsaturation.

The method of preparation of the compound presented by formula (I) is described in Japanese Laid Open Patent Application Nos. 62-228048/1987, 63-216852/1988 and in the U.S. Pat. No. 4,778,823.

The amphiphatic lipids described above can be used individually or in combination. When the combination of amide derivative (I) and another amphiphatic lipid is used, it is preferable that the ratio be in the range of 100/1-1/100, and more preferably 10/1-1/10.

Amphiphatic compounds are incorporated in the present cosmetic composition in an amount of 0.05-30% by weight, preferably 0.1-10% by weight based on the total composition.

Suitable nonionic surfactants (B) for use in the present composition include, surfactants with polyoxyethylene, for example, polyoxyethylene hydrogenated castor oil; polyoxyethylene sorbitan fatty acid ester, such as polyoxyethylene sorbitan monostearate, polyoxyethylene sorbitan tetraoleate; polyoxyethylene glyceryl fatty acid ester, such as polyoxyethylene glyceryl monoisostearate, polyoxyethylene glyceryl triisostearate; polyoxyethylene glycol fatty acid ester, such as polyoxyethylene glycol monoisostearate; polyoxyethylene alkyl ether, such as polyoxyethylene hexyl decyl ether, polyoxyethylene octyl dodecyl ether, polyoxyethylene lauryl ether, polyoxyethylene cetyl ether, polyoxyethylene stearyl ether, polyoxyethylene oleyl ether, polyoxyethylene nonyl phenyl ether.

Other nonionic surfactants, such as polyglycerine alkyl ether, polyglycerine fatty acid ester, sucrose fatty acid ester are also usable.

Preferred surfactants are polyoxyethylene hydrogenated castor oil or a polyoxyethylene alkyl ether having HLB 8 to 20, preferably 10–16. These nonionic surfactants may be used individually or in combination, so long as the total has an HLB of 8 to 20.

The cosmetic composition of this invention contains 0.05–30% by weight, preferably 0.1–10% by weight of (B) based on the total composition.

Ionic surfactant(s) used in this invention are anionic surfactants, amphoteric surfactants or cationic surfactants.

Suitable anionic surfactants for use in the present composition include polyoxyethylene alkyl sulphate, such as sodium polyoxyethylene lauryl sulphate, polyoxyethylene lauryl sulphate triethanol amine; N-acyl amino acids such as sodium lauroyl sarcocin, sodium lauroyl methylalanine; polyoxyethylene alkyl ether phosphates, such as sodium polyoxyethylene lauryl ether phosphate, sodium polyoxyethylene cetyl ether phosphate, dipolyoxyethylene alkyl ether phosphates, tripolyoxyethylene alkyl ether phosphates, dipolyoxyethylene phenyl ether phosphates, sodium polyoxyethylene lauryl ether phosphate, sodium dipolyoxyethylene lauryl ether phosphates.

Suitable amphoteric surfactants for use in the present composition include alkylbetaine, alkylaminobetaine, alkylsulphobetaine.

Suitable cationic surfactants for use in the present composition include the di-long chain alkyl quaternary ammonium salt, mono-long chain alkyl quaternary ammonium salt, di-long chain alkyl polyoxyethylene ammonium salts, mono-long chain alkyl polyoxyethylene ammonium salts, bis-(hydroxyalkyl) quaternary ammonium salt, quaternary ammonium salts having an amide bond or ester bond, which can be used alone or in combination.

Component (C) is used in an amount of 1–50% by weight, preferably 2–30% by weight based on the weight of component (B). If the amount of the (C) is out of this range, the cosmetic composition will not be adequately transparent or semi-transparent.

Components (A), (B), and (C) are incorporated in the cosmetic composition in the ratio of (A)/[(B)+(C)]=0-.2–10, preferably 0.5–2. If the ratio of (A)/[(B)+(C)] is less than 0.2, the relative amount of surfactant will be so large that the composition may become transparent, but the irritation to the skin will be a potential problem. If the ratio of (A)/[(B)+(C)] is larger than 10, the composition also will not be adequately transparent or semi-transparent.

Suitable aqueous medium (D) for use in the present composition include water, or a combination of water and an aqueous alcohol, such as ethanol, glycerine, sorbitol, propyleneglycol, dipropyleneglycol, 1,3-butanediol.

Component (D) may be used in an amount of 40–99% by weight, preferably 80–95% by weight, based on the total composition.

Typical cosmetic ingredients as are usually present in cosmetics may be present here as well, including oils, silicone oils, polyols, water soluble polymers, UV-ray absorbers, antiseptics, perfumes, ethanol, inorganic or organic powders, germicides, colorants and the like.

It is best if a large amount of oil not be used in the present composition. The maximum should be about 2% by weight.

While the cosmetic composition of this invention are beautifully transparent or semi-transparent, a latex or other reagent can be added to increase the turbidity, if desired.

It is also possible to incorporate an ethyleneglycol ester to obtain pearl-like product.

The composition of this invention is produced as follows:

Components (A), (B) and/or (C) are mixed and melted at temperatures of 65°–95° C. and then aqueous (D) is added thereto. An anisotropic liquid crystal phase is formed which, after cooling to room temperature a lipid microdispersion is obtained which is suitable for cosmetic composition applications.

In this process, it is preferable that polyols such as glycerine be incorporated into the lipids and surfactants mixture (A), (B), (C), to produce effectively the lipid microdispersion system.

EXAMPLES

The present invention will be described in detail by way of the following examples. The present invention, however, is not limited to these examples.

EXAMPLES 1–28

The components except water, in the Table 1 to 3, were mixed and melted at a temperature of 85°–90° C. Hot water was added, and the composition was cooled to produce a lotion. The lotion obtained was transparent or semi-transparent depending upon the particular ratios.

TABLE 1

|  | Examples | | | | | | | | | | | (% by weight) |
|---|---|---|---|---|---|---|---|---|---|---|---|---|
|  | 1 | 2 | 3 | 4 | 5 | 6 | 7 | 8 | 9 | 10 | 11 | 12 |
| Polyoxyethylene hydrogenated castor oil | | | | | | | | | | | | |
| (5E.O) | | | | | | 0.33 | | | | | | |
| (10E.O) | | | | 1.39 | | 0.83 | | | | | | |
| (20E.O) | | | | | | | | 0.89 | | | | |
| (30E.O) | 2.5 | | | | | | | 0.89 | 1.00 | | | |

TABLE 1-continued (% by weight)

| | Examples | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| (40E.O) | | 2.5 | | | | | | | 1.7 | 2.1 | 3.75 | 2.5 |
| (50E.O) | | | 2.5 | | 2.17 | 1.67 | 1.61 | 1.50 | | | | |
| (80E.O) | | | | 1.11 | | | | | | | | |
| Sodium polyoxyethylene lauryl ether phosphate (4E.O) | 0.5 | 0.5 | 0.5 | 0.5 | 0.5 | 0.5 | 0.5 | 0.5 | 0.3 | 0.4 | 0.75 | 0.5 |
| Amide derivative $R^1 = C_{16}H_{33}$, $R^2 = C_{15}H_{31}$ | 3.0 | 3.0 | 3.0 | 3.0 | 3.0 | 3.0 | 3.0 | 3.0 | 3.0 | 3.0 | 3.0 | 1.65 |
| Anticeptics | 0.3 | 0.3 | 0.3 | 0.3 | 0.3 | 0.3 | 0.3 | 0.3 | 0.3 | 0.3 | 0.3 | 0.3 |
| 86% Glycerin | 5.0 | 5.0 | 5.0 | 5.0 | 5.0 | 5.0 | 5.0 | 5.0 | 5.0 | 5.0 | 5.0 | 5.0 |
| Water | bal. | bal. | bal. | bal. | bal. | bal. | bal. | bal. | bal. | bal. | bal. | bal. |

TABLE 2

(% by weight)

| | Examples | | | | | | | |
|---|---|---|---|---|---|---|---|---|
| | 13 | 14 | 15 | 16 | 17 | 18 | 19 | 20 |
| Polyoxyethylene hydrogenated caster oil (40E.O) | 2.5 | | | | | | | |
| Polyoxyethylene lauryl ether (9E.O) | | | | 0.5 | | | | |
| Polyoxyethylene lauryl ether (23E.O) | | | 2.5 | 0.5 | | | | |
| Polyoxyethylene isocetyl ether (20E.O) | | 2.5 | | 1.5 | | | | |
| Polyoxyethylene cetyl ether (13E.O) | | | | | 2.5 | | | |
| Polyoxyethylene stearyl ether (12E.O) | | | | | | 2.5 | | |
| Polyoxyethylene oleyl ether (13E.O) | | | 2.5 | | | | 2.5 | |
| Polyoxyethylene monoisostearate (14E.O) | | | | | | | | 2.5 |
| Sodium polyoxyethylene lauryl ether phosphate (4E.O) | 0.5 | 0.5 | 0.5 | 0.5 | 0.5 | 0.5 | 0.5 | 0.5 |
| Amide derivative [$R^1 = C_{16}H_{33}$, $R^2 = C_{15}H_{31}$] | 1.8 | 1.6 | 1.6 | 1.6 | 1.6 | 1.6 | 1.6 | 3.0 |
| Squalene | | 1.4 | 1.4 | 1.4 | 1.4 | 1.4 | 1.4 | |
| Cetanol | 0.72 | | | | | | | |
| Stearyl alcohol | 0.48 | | | | | | | |
| 86% Glycerin | 7.0 | 5.5 | 5.5 | 5.5 | 5.5 | 5.5 | 5.5 | 3.0 |
| 55% Ethanol | | 20.0 | 20.0 | 20.0 | 20.0 | 20.0 | 20.0 | 20.0 |
| Water | bal. | bal. | bal. | bal. | bal. | bal. | bal. | bal. |

TABLE 3

(% by weight)

| | Examples | | | | | | | |
|---|---|---|---|---|---|---|---|---|
| | 21 | 22 | 23 | 24 | 25 | 26 | 27 | 28 |
| Polyoxyethylene hydrogenated caster oil (40E.O) | 2.5 | 2.5 | 2.5 | 2.5 | 2.5 | 2.5 | 2.5 | 2.5 |
| Sodium polyoxyethylene lauryl ether phosphate (4E.O) | 0.1 | 0.3 | | | | | | 0.3 |
| Sodium polyoxyethylene cetyl ether phosphate (5E.O) | | | 0.5 | | | | | |
| Dipolyoxyethylene alkyl ether phosphate (4E.O) | | | | | | | | 0.2 |
| Sodium polyoxyethylene lauryl ether sulphate | | | | 0.5 | | | | |
| Polyoxyethylene lauryl ether sulphate triethanol amine | | | | | 0.5 | | | |
| Sodium lauroyl sarcocin | | | | | | 0.5 | | |
| Sodium lauroyl methylalanine | | | | | | | 0.5 | |
| Amide derivative [$R^1 = C_{16}H_{33}$, $R^2 = C_9H_{19}$] | 1.65 | 1.65 | 1.65 | 1.65 | 1.65 | 1.65 | 1.65 | 1.65 |
| Cholesterol | 0.45 | 0.45 | 0.45 | 0.45 | 0.45 | 0.45 | 0.45 | 0.45 |
| Stearic acid | 0.33 | 0.33 | 0.33 | 0.33 | 0.33 | 0.33 | 0.33 | 0.33 |
| Parmitic acid | 0.27 | 0.27 | 0.27 | 0.27 | 0.27 | 0.27 | 0.27 | 0.27 |
| Cholesteryl isostearate | 0.30 | 0.30 | 0.30 | 0.30 | 0.30 | 0.30 | 0.30 | 0.30 |
| Glycerin | 5.0 | 5.0 | 5.0 | 5.0 | 5.0 | 5.0 | 5.0 | 5.0 |
| Water | bal. | bal. | bal. | bal. | bal. | bal. | bal. | bal. |

We claim:

1. A cosmetic composition comprising:
   (A) 0.05-30% by weight of an amphipathic lipid selected from the group consisting of a ceramide, a derivative of a ceramide, a glycolipid, a derivative of a glycolipid, and a mixture thereof,
   (B) 0.05-30% by weight of a nonionic surfactant,
   (C) 1-50% by weight, based on (B), of an ionic surfactant, and
   (D) 40-99% by weight of an aqueous medium,
   wherein said composition is transparent or semi-transparent, and wherein the ratio of (A)/[(B) (C)] is 0.2-10.

2. The cosmetic composition of claim 1 wherein said ionic surfactant is present in an amount of 2-30% based on (B).

3. The cosmetic composition of claim 1 wherein said nonionic surfactant is present in an amount of 0.1-10%.

4. The cosmetic composition of claim 1 wherein said ionic surfactant is present in an amount of 2-30% based on (B).

5. The cosmetic composition of claim 1 wherein said amphipatic lipid is the combination of an amide of the formula (I) and another amphipathic lipid.

6. The cosmetic composition of claim 1 wherein said nonionic surfactant is a polyoxyethylene alkyl ether having a HLB of 8 to 20.

7. The cosmetic composition of claim 1 wherein said nonionic surfactant is selected from the group consisting of polyoxyethylene hydrogenated castor oil, polyoxyethylene lauryl ether, polyoxyethylene isocetyl ether, polyoxyethylene cetyl ether, polyoxyethylene stearyl ether, polyoxyethylene oleyl ether, and polyoxyethylene monoisostearate.

8. The cosmetic composition of claim 1 wherein said ionic surfactant is a polyoxyethylene alkyl phosphate.

9. The cosmetic composition of claim 1 wherein said ionic surfactant is a polyoxyethylene alkyl sulphate.

10. The cosmetic composition of claim 1 wherein said ionic surfactant is an N-acyl amino acid.

11. The cosmetic composition of claim 1 wherein said ionic surfactant is selected from the group consisting of sodium polyoxyethylene lauryl ether phosphate, sodium polyoxyethylene cetyl ether phosphate, dipolyoxyethylene alkyl ether phosphate, sodium polyoxyethylene lauryl ether sulphate, polyoxyethylene lauryl ether sulphate triethanol amine, sodium lauroyl sarcocin, and sodium lauroyl methylalanin.

12. The cosmetic composition of claim 1 wherein said ratio of (A)/[(B)+(C)] is 0.5-2.

13. The cosmetic composition of claim 1 wherein said amphiphatic lipid is present in an amount of 0.1-10%.

14. A cosmetic composition comprising:

(A) 0.05-50% by weight of an amphipathic lipid of the formula (I):

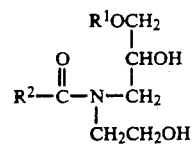

wherein
$R^1$ is a hydrocarbon having 10-26 carbon atoms, and
$R^2$ is a hydrocarbon having 9-25 carbon atoms;
(B) 0.05-30% by weight of a nonionic surfactant;
(C) 1-50% by weight, based on (B), of an ionic surfactant, and
(D) 40-99% by weight of an aqueous medium, wherein said composition is transparent or semi-transparent, and wherein the ratio (A)/[(B)+(C)] is 0.2-10.

15. The cosmetic composition of claim 14, wherein said ionic surfactant is present in an amount of 2-30% based on (B).

16. The cosmetic composition of claim 14, wherein said nonionic surfactant is present in an amount of 0.1-10%.

17. The cosmetic composition of claim 14, wherein said ionic surfactant is present in an amount of 2-30% based on (B).

18. The cosmetic composition of claim 14, wherein said amphipathic lipid of formula (I) further comprises another amphipathic lipid.

19. The cosmetic composition of claim 14, wherein said ratio of (A)/[(B)+(C)] is 0.5-2.

20. The cosmetic composition of claim 14, wherein said amphipathic lipid of the formula (I) is present in an amount of 0.1-10%.

* * * * *